US009670519B2

(12) United States Patent
Srivastava et al.

(10) Patent No.: US 9,670,519 B2
(45) Date of Patent: Jun. 6, 2017

(54) METHODS FOR REDUCING ACCUMULATION OF LACTATE DURING CULTURING AND METHOD FOR PRODUCING POLYPEPTIDE (75) Inventors: Ruchika Srivastava, Bangalore (IN); Sneha Lakshmandas Hemdev, Bangalore (IN); Ankur Bhatnagar, Bangalore (IN); Saravanan Desan, Bangalore (IN); Anuj Goel, Bangalore (IN); Harish Iyer, Bangalore (IN); Vana Raja, Hosur (IN); Lavanya Rao, Bangalore (IN)

(73) Assignee: Biocon Limited, Bangalore (IN)

( * ) Notice: Subject to any disclaimer, the term of this patent is extended or adjusted under 35 U.S.C. 154(b) by 0 days.

(21) Appl. No.: 14/114,525

(22) PCT Filed: Apr. 27, 2012

(86) PCT No.: PCT/IB2012/052108
§ 371 (c)(1),
(2), (4) Date: Nov. 1, 2012

(87) PCT Pub. No.: WO2012/147048
PCT Pub. Date: Nov. 1, 2012

(65) Prior Publication Data
US 2014/0051124 A1    Feb. 20, 2014

(30) Foreign Application Priority Data

Apr. 29, 2011    (IN) .......................... 1486/CHE/2011

(51) Int. Cl.
*C12P 21/00* (2006.01)
*C07K 16/28* (2006.01)
*C12N 5/00* (2006.01)

(52) U.S. Cl.
CPC .......... *C12P 21/00* (2013.01); *C07K 16/2863* (2013.01); *C07K 16/2866* (2013.01); *C07K 16/2896* (2013.01); *C12N 5/0018* (2013.01); *C12N 2500/10* (2013.01)

(58) Field of Classification Search
None
See application file for complete search history.

(56) References Cited

U.S. PATENT DOCUMENTS

| 6,156,570 A | 12/2000 | Hu |
| 7,429,491 B2 | 9/2008 | Luan |
| 2003/0087372 A1* | 5/2003 | DeLaCruz ............... C07K 16/00 435/69.1 |
| 2011/0104734 A1 | 5/2011 | Croughan |

FOREIGN PATENT DOCUMENTS

WO    2008109410 A1    9/2008

OTHER PUBLICATIONS

Russell, Brian A., et al. "Identification of copper as the root cause of lactate differences between raw materials sourced from different vendors." 2010, Abstracts of Papers of the American Chemical Society. 1155 16th St, NW, Washington, DC 20036 USA: Amer Chemical Soc, vol. 239., entire abstract.*
Gagnon et al., High-End pH-controlled delivery of glucose effectively suppresses lactate accumulation in CHO Fed-batch cultures, 2011, Biotechnology and Bioengineering 108(6): 1328-1337.*
Smith, Paul J., et al. "Impact of overexpression of metallothionein-1 on cell cycle progression and zinc toxicity." American Journal of Physiology-Cell Physiology 295.5 (2008): C1399-C1408.*
Monia, B. P., et al. "Metallothionein turnover in mammalian cells. Implications in metal toxicity." Journal of Biological Chemistry 261.24 (1986): 10957-10959.*
Lee, T. C., et al. "Elevation of glutathione levels and glutathione S-transferase activity in arsenic-resistant Chinese hamster ovary cells." In vitro cellular & developmental biology 25.5 (1989): 442-448.*
Thermo Scientific HyClone Product listing, entitled "Thermo Scientific HyClone Media Cell Culture Products and Capabilities." 2010, p. 35-40.*
PCT International Search Report mailed on Dec. 13, 2012 from corresponding PCT Application No. PCT/IB2012/052108.
PCT Written Opinion mailed on Dec. 13, 2012 from corresponding from corresponding PCT Application No. PCT/IB2012/052108.
PCT Chapter II International Preliminary Report on Patentability dated Apr. 16, 2013 from corresponding from corresponding PCT Application No. PCT/IB2012/052108.
Borchardt, T. et al., "Differential effects of zinc on amyloid precursor protein (APP) processing in copper-resistant variants of cultured Chinese hamster ovary cells", Cellular and Molecular Biology, 2000, vol. 46, pp. 785-795.
Chaderjian, W.B. et al., "Effect of Copper Sulfate on Performance of a Serum-Free CHO Cell Culture Process and the Level of Free Thiol in the Recombinant Antibody Expressed" Biotechnology Progress, 2005, vol. 21, pp. 550-553.
Luo, J. et al., "Comparative Metabolite Analysis to Understand Lactate Metabolism Shift in Chinese Hamster Ovary Cell Culture Process", Biotechnology and Bioengineering, 2012, vol. 109, pp. 146-156 (published online Sep. 30, 2011).
Pelletier, B. et al., "Effect of copper sulfate addition on the growth and productivity of a serum-free CHO cell culture producing a recombinant antibody" Abstracts of Papers, 229th ACS National Meeting, 2005, Abstract BIOT 232.

(Continued)

*Primary Examiner* — Robert Yamasaki
(74) *Attorney, Agent, or Firm* — Schwegman Lundberg & Woessner, P.A.

(57) ABSTRACT

The present disclosure relates to methods of decreasing lactate production in cell culture using divalent transitional metallic salts. The present disclosure also relates to a method of producing polypeptide by adding divalent transitional metallic salt to the cell culture medium for reducing lactate accumulation followed by fermenting and recovering the polypeptide.

4 Claims, 6 Drawing Sheets

(56) References Cited

OTHER PUBLICATIONS

Qian, Y. et al., "Cell Culture and Gene Transcription Effects of Copper Sulfate on Chinese Hamster Ovary Cells", Biotechnology Progress, 2011, vol. 27, pp. 1190-1194 (published online May 18, 2011).

Russell, B.A. et al., "Identification of copper as the root cause of lactate differences between raw materials sourced from different vendors" Abstracts of Papers, 239th ACS National Meeting, 2010, Abstract BIOT 498.

Zhou, M. et al., "Decreasing lactate level and increasing antibody production in Chinese Hamster Ovary cells (CHO) by reducing the expression of lactate dehydrogenase and pyruvate dehydrogenase kinases", Journal of Biotechnology, 2011, vol. 153, pp. 27-34 (published online Mar. 8, 2011).

* cited by examiner

METHODS FOR REDUCING ACCUMULATION OF LACTATE DURING CULTURING AND METHOD FOR PRODUCING POLYPEPTIDE

CROSS-REFERENCE TO RELATED APPLICATIONS

This application is the U.S. National Stage of International Patent Application No. PCT/IB2012/052108, filed on Apr. 27, 2012, which claims priority to Indian Patent Application No. 1486/CHE/2011 filed on Apr. 29, 2011, the disclosures of which are hereby incorporated by reference in their entireties.

TECHNICAL FIELD

The present disclosure relates to method for reducing accumulation of lactate in a cell culture, said method comprising act of adding using divalent transitional metallic salt to the cell culture. The present disclosure also relates to a method for producing polypeptide, said method comprising acts of adding divalent transitional metallic salt to the cell culture medium for reducing lactate accumulation and fermenting and recovering the polypeptide. More specifically the disclosure relates to a method of growing cells in a cell culture system that reduces accumulation of lactate in the culture medium.

BACKGROUND AND PRIOR ART OF THE DISCLOSURE

Animal cell culture technologies are widely used in biomedical research and pharmaceutical industry. Assessment of cell growth and metabolic activities are essential to the success in the control and improvement of cell culture process. Two of the most commonly monitored metabolites are glucose and lactate. Glucose serves as both a main carbon source and an important energy source in most medium formulation. Entry of glucose into glycolytic pathway leads to the formation of pyruvate as the end product. In animal cells, pyruvate can either be shuttled into the TCA cycle or be converted into lactate. Due to the high flux of glucose to pyruvate and the inefficient coupling between glycolysis and TCA cycle, lactate accumulation tends to occur in continuous cell cultures. Lactate build-up in turn will lead to the acidification of the culture environment. In addition, lactate itself could also be toxic to mammalian cells even under controlled pH. The accumulation of lactate is often a critical limiting factor of a cell culture process especially when the cell density is high.

In biopharmaceutical manufacturing, monitoring glucose and lactate has become a routine practice due to the simplicity and reliability of measurement as well as their chemical stability in culture medium. More importantly, glucose concentration provides an assessment of energy while lactate is considered an important parameter for the accumulation of metabolic byproducts and an indicator of a deteriorating culture environment. As critical culture parameters, glucose and lactate measurements are often the key components in the design for process control in bioreactor operations such as feeding or perfusion strategies.

Significant effort has been made in the past to correlate glucose and lactate metabolism with cell density. The consumption rate of glucose and the accumulation rate of lactate reflect metabolic activities of cultured cells.

As stated earlier accumulation of toxic byproducts such as lactate have an inhibitory effect on cell growth and antibody production. Excessive lactate buildup can result in increased medium osmolarity or, in the absence of pH control, decreased culture pH. The major negative effect of lactate is caused by the decrease in pH that follows from its excretion to the culture medium.

U.S. Pat. No. 6,156,570 teaches process for cultivating cells, preferably mammalian cells, that minimizes the accumulation of lactate.

U.S. Pat. No. 7,429,491 teaches method of improving protein production in animal cell culture using restricted glucose in the fed batch culture.

In the past, attempts have been made to reduce the lactate levels mainly by A] feeding and maintaining a very low level glucose or B] by metabolic engineering of the cells using molecular biology techniques.

This work reveals the correlation between the addition of divalent transitional metal salts (Copper, Zinc) and lactate accumulation and of the possible ways of reducing the same.

STATEMENT OF THE DISCLOSURE

Accordingly, the present disclosure relates to a method for reducing accumulation of lactate in a cell culture, said method comprising act of adding divalent transitional metal salt to the cell culture and a method for producing polypeptide, said method comprising acts of a) adding divalent transitional metal salt to cell culture for reducing lactate accumulation and b) fermenting and recovering the polypeptide.

DETAILED DESCRIPTION OF THE DISCLOSURE

The present disclosure relates to a method for reducing accumulation of lactate in a cell culture, said method comprising act of adding divalent transitional metal salt to the cell culture.

In an embodiment of the present disclosure, the divalent transitional metal salt is having metal selected from a group comprising copper and zinc.

In an embodiment of the present disclosure, the copper salt is copper sulphate and the zinc salt is Zinc sulphate.

In another embodiment of the present disclosure, the cell is obtained from mammalian cell line.

In another embodiment of the present disclosure, the mammalian cell line is selected from a group comprising but not limiting to Chinese Hamster Ovary (CHO) cells, NS0 (non secreting 0) and BHK (baby hamster kidney).

In another embodiment of the present disclosure, the divalent transitional metal ion is added at a concentration ranging from about 0.2 mM to about 0.4 mM.

In another embodiment of the present disclosure, the culturing is carried out in a system selected from a group comprising but not limiting to fed batch culturing, batch culturing, shake flasks and bioreactor.

In another embodiment of the present disclosure, the reduction in accumulation of lactate level is from about 5% to about 40%.

The present disclosure also relates to a method for producing polypeptide, said method comprising acts of adding divalent transitional metal salt to cell culture for reducing lactate accumulation and fermenting and recovering the polypeptide.

In another embodiment of the present disclosure, the cells are obtained from mammalian cell line.

In another embodiment of the present disclosure, the mammalian cell line is selected from a group comprising but not limiting to Chinese Hamster Ovary (CHO) cells, NS0 and BHK.

In another embodiment of the present disclosure, the divalent transitional metallic salt is having metal selected from a group comprising copper and zinc.

In another embodiment of the present disclosure, the copper salt is copper sulphate and the zinc salt is Zinc sulphate.

In another embodiment of the present disclosure, the salt is added at a concentration ranging from about 0.2 mM to about 0.4 mM.

In another embodiment of the present disclosure, the polypeptide is selected from a group comprising but not limited to Anti VEGF-A Antibody, Anti Her-2 Antibody, Anti CD6 Antibody and Anti TNF antibody.

In another embodiment of the present disclosure, the culturing process is carried out in any a system selected from a group comprising but not limiting to fed batch culturing, batch culturing, shake flasks and bioreactor.

In an embodiment of the present disclosure, the present disclosure relates to methods of decreasing lactate accumulation utilizing a modified cell culture method comprising a cell growth phase and a polypeptide production phase.

Accordingly present disclosure provides process for the production of the polypeptides, exemplified by way of monoclonal antibody, by a process with reduced lactate accumulation.

Further disclosure states reducing lactate accumulation is reduced in the range from about 5% to about 40%.

The present disclosure relates to a process for the production of the monoclonal antibody by a process with reduced lactate accumulation.

In an embodiment of the present disclosure, wherein lowering the amount of lactate accumulation that is normally associated with standard production procedure.

In another embodiment of the present disclosure, a process is described in which addition of divalent transitional metallic salts decreases the accumulation of lactate in the fed-batch system.

In an embodiment of the present disclosure, the divalent transitional metallic salt includes Zinc and Copper salts.

In yet another embodiment of the present disclosure, the concentration of zinc and copper salts used in the culture medium is about 0.4 mM.

In another embodiment of the present disclosure, the divalent transitional metallic salt of copper is copper sulphate and the metallic salt of Zinc is Zinc sulphate.

In another embodiment of the present disclosure, the concentration of the divalent transitional metallic salts is mentioned as concentration of the salt in the culture medium.

In another embodiment of the present disclosure, these Zinc and Copper metal ions are required for the activity of the enzymes involved in Glycolysis & TCA pathway and therefore, the addition of these ions improves the overall metabolic efficiency of cells making most of the glucose getting completely oxidized, so the accumulation of lactate is reduced.

In another embodiment of the present disclosure, the media is a chemically defined media which is selected from a group comprising but not limited to and HyClone CDM4NS0 and HyClone CDM4Mab.

In another embodiment of the present disclosure, the mammalian cells can be selected from a group comprising but not limited to Chinese Hamster Ovary (CHO) cells, Non Secreting 0 (NS0) and Baby Hamster Kidney (BHR).

In another embodiment of the present disclosure, the polypeptide can be selected from a group comprising but not limited to Anti VEGF-A Antibody, Anti Her-2 Antibody, Anti CD6 Antibody and Anti TNF antibody.

In another embodiment of the present disclosure, the level of lactate in the medium is analyzed using the device YSI 7100 MBS Analyzer.

In another embodiment of the present disclosure, the reduction in lactate accumulation leads to overall better culture performance as the overall ph maintenance, cell maintenance is better. The addition of divalent transitional metallic salts eg. Zinc/Copper salts reduces the lactate accumulation and therefore, the pH of the medium is also maintained.

In an embodiment of the present disclosure, the divalent transitional metal salt can also be defined as divalent transitional metal ions.

In another embodiment of the present disclosure, the present disclosure also relates to method of improving protein production, e.g. large scale commercial protein production, e.g. antibody production.

In another embodiment of the present disclosure, the present disclosure also relates to methods of growing cells in a cell culture system that reduces accumulation of lactate in the culture medium.

In another embodiment of the present disclosure, the addition of divalent transitional metallic salts i.e., Zinc/Copper salts further enhances the reduction of lactate accumulation from about 5% to about 40%.

DEFINITION OF TERMS

In describing and claiming the present disclosure, the following terminology will be used in accordance with the definitions set out herein.

The term "antibody" includes antibodies or antibody derivatives or fragments thereof and the specifications of the antibodies also apply to the antibody preparation of the present disclosure. Among the antibody fragments functional equivalents or homologues of antibodies including any polypeptide comprise an immunoglobulin binding domain or peptides mimicking this binding domain together with an Fc region or a region homologous to a Fc region or at least part of it. Chimeric molecules comprising an immunoglobulin binding domain, or equivalents, fused to another polypeptide are included.

Exemplary antibody molecules are intact immunoglobulin molecules and those portions of an immunoglobulin molecule that contains the paratope, including those portions known as Fab, Fab', F(ab')2, Fc and F(v), as well as the N-glycan structure.

Antibody describes a functional component of serum and is often referred to either as a collection of molecules (antibodies or immunoglobulins, fragments, etc.) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or on distinct, different antigens). The distinct and different antibody molecules constituting a polyclonal antibody may be termed "members". Each antibody molecule has a unique structure that enables it to bind specifically to its corresponding antigen, and all natural antibody molecules have the same overall basic structure of two identical light chains and two identical heavy chains.

As used herein, the phrases "polypeptide" or "polypeptide product" are synonymous with the terms "protein" and "protein product," respectively, and, as is generally understood in the art, refer to at least one chain of amino acids linked via sequential peptide bonds. In certain embodiments, a "protein of interest" or a "polypeptide of interest" or the like is a protein encoded by an exogenous nucleic acid molecule that has been transformed into a host cell. In certain embodiments, wherein an exogenous DNA with which the host cell has been transformed codes for the "protein of interest," the nucleic acid sequence of the exogenous DNA determines the sequence of amino acids. In certain embodiments, a "protein of interest" is a protein encoded by a nucleic acid molecule that is endogenous to the host cell. In certain embodiments, expression of such an endogenous protein of interest is altered by transfecting a host cell with an exogenous nucleic acid molecule that may, for example, contain one or more regulatory sequences and/or encode a protein that enhances expression of the protein of interest.

As used herein, "antibody variant" refers to an antibody which has an amino acid sequence which differs from the amino acid sequence of a parent antibody. Preferably, the antibody variant comprises a heavy chain variable domain or a light chain variable domain having an amino acid sequence which is not found in nature. Such variants necessarily have less than 100% sequence identity or similarity with the parent antibody. In a preferred embodiment, the antibody variant will have an amino acid sequence from about 75% to less than 100% amino acid sequence identity or similarity with the amino acid sequence of either the heavy or light chain variable domain of the parent antibody, more preferably from about 80% to less than 100%, more preferably from about 85% to less than 100%, more preferably from about 90% to less than 100%, and most preferably from about 95% to less than 100%. Identity or similarity with respect to this sequence is defined herein as the percentage of amino acid residues in the candidate sequence that are identical (i.e. same residue) with the parent antibody residues, after aligning the sequences and introducing gaps, if necessary, to achieve the maximum percent sequence identity.

The terms "media", "medium," "cell culture medium," and "culture medium" as used herein refer to a solution containing nutrients that nourish growing animal cells, e.g., mammalian cells, and can also refer to medium in combination with cells.

The preferred mammalian hosts are Chinese Hamster Ovary (CHO) cells. Methods and vectors for genetically engineering cells and/or cell lines to express a protein of interest are well known to those skilled in the art. Genetic engineering techniques include but are not limited to expression vectors, targeted homologous recombination and gene activation. Optionally, the proteins are expressed under the control of a heterologous control element such as, for example, a promoter that does not in nature direct the production of that polypeptide. For example, the promoter can be a strong viral promoter (e.g., CMV, SV40) that directs the expression of a mammalian polypeptide. The host cell may or may not normally produce the protein. For example, the host cell can be a CHO cell that has been genetically engineered to produce a protein, meaning that nucleic acid encoding the protein has been introduced into the CHO cell.

Lactate, a by-product generated during mammalian cell growth that is potentially toxic to the cells. Accumulation of lactate impacts buffering capacity of media resulting in decrease of pH. It has been shown that lactate negatively affects not only cell growth and productivity, but overall product quality as well. Several approaches have been attempted to reduce lactate accumulation in culture media. They include cell growth under low glucose concentration, over expression of pyruvate decarboxylase and knock-out of the Lactate Dehydogenase-A (LDH-A) gene.

The following examples show how the process can be manipulated by addition of certain divalent transitional metallic salts to reduce the lactate accumulation in the process. Lactate reduces by almost 5-40% throughout the run.

In an embodiment of the present disclosure, the divalent transitional metal salt can also be defined as divalent transitional metal ions.

In an embodiment of the present disclosure, the conventionally known techniques to separate proteins/antibodies from culture Medias which can be used are ion exchange chromatography, gel filtration chromatography and affinity chromatography.

In another embodiment of the present disclosure, the affinity chromatography technique has been used as a preferred technique to separate the antibodies from the media.

The foregoing descriptions of specific embodiments of the present disclosure are presented for purposes of illustration and description. They are not intended to be exhaustive or to limit the disclosure to the precise forms disclosed. Various modifications and variations are possible in view of the above teachings. In addition, many modifications may be made to adapt a particular situation, material, composition of matter, process, process step or steps, to the objective, spirit and scope of the present disclosure. All such modifications are intended to be within the scope of the claims appended hereto.

The technology of the instant Application is further elaborated with the help of following examples. However, the examples should not be construed to limit the scope of the disclosure.

EXAMPLES

The level of lactate is analyzed for all the following experiments in the below examples by the use of the YSI 7100 MBS Analyzer. The pH for all the below experiments as recited in the following examples are maintained between pH 6.85-7.2. The level of Oxygen is also maintained by the oxygen levels are maintained by agitation in the shaker incubator. In all the below mentioned examples, the concentration of the added salt is the concentration of the salt as present in the medium. The temperature can be suitably varied, based on the nature of the cells used and other related parameters.

Two divalent transitional metallic salts have been used in carrying out the present invention. The two divalent transitional metallic salts are copper sulphate pentahydrate and zinc sulphate hepta hydrate.

Example 1

Example 1(A)

The cell culturing was performed in fedbatch mode. In the cell culture, the mammalian host cells used were Chinese Hamster Ovary (CHO) cells and HyClone CDM4NS0 culture medium was supplied initially. The CHO cells were genetically engineered to produce the Anti VEGF-A antibody. The copper sulphate pentahydrate salt was added in the medium at a concentration of 0.4 mM. In contrast, there was no addition of any copper salt in the control medium. The production fermentation run started with an initial cell count of 0.3-0.45×10$^6$ cells/ml at 37±1° C., the first 3-4 days were dedicated to grow the cells in batch phase. In the next step, the temperature is lowered to 31+/−1° C. and the run is continued till 7$^{th}$ day. The below table 1 discloses the level of lactate reduced throughout the run. The produced Anti VEGF-A antibody was then collected from the media using the technique of Affinity Chromatography.

TABLE 1

| Age (in hours) | Control - Residual Lactate (mM) | With Copper salt - Residual Lactate (mM) |
| --- | --- | --- |
| 72 | 18 | 16 |
| 96 | 17.2 | 14.8 |
| 120 | 11.1 | 5.9 |
| 144 | 8 | 3.4 |
| 168 | 7 | 2 |

The control reduced the accumulation of lactate by about 61%, whereas the media with the added salt reduced the accumulation of lactate by about 87.5%. The present example showed further reduction in the accumulation of lactate by about 26.5% in presence of said salt.

Figure 1A:
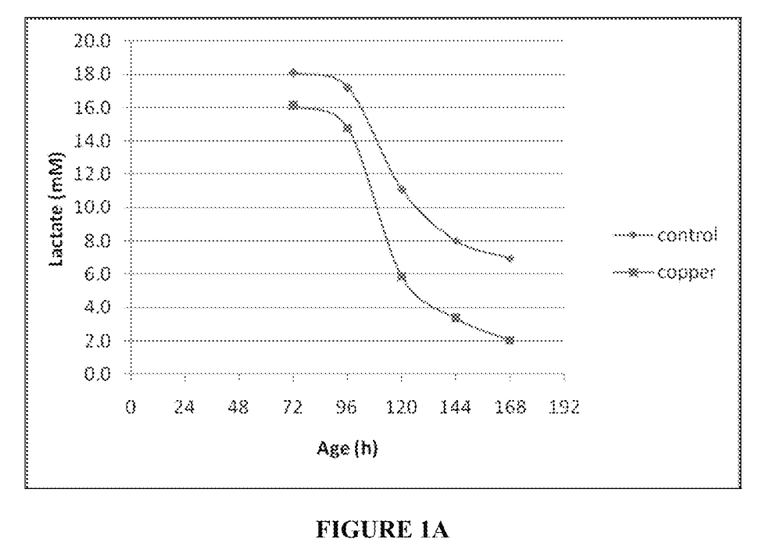
FIG. 1A illustrates the difference in level of lactate accumulation in the presence of Copper salt Vs Control.

FIG. 1(A) illustrates the level of reduction in lactate in the culture medium.

Example 1(B)

The cell culturing was performed in fedbatch. In the cell culture, the mammalian host cells used were Chinese Hamster Ovary (CHO) cells and HyClone CDM4NS0 culture medium was supplied initially. The CHO cells were genetically engineered to produce the Anti VEGF-A antibody. The zinc sulphate hepta hydrate salt was added in the medium at a concentration of 0.4 mM. In contrast, there was no addition of any zinc salt in the control medium. The production fermentation run started with an initial cell count of 0.3-0.45×10$^6$ cells/ml at 37±1° C., the first 3-4 days were dedicated to grow the cells in batch phase. In the next step, the temperature is lowered to 31+/−1° C. and the run is continued till 7$^{th}$ day. The below table 2 discloses the level of lactate is reduced throughout the run. The produced Anti VEGF-A antibody was then collected from the media using the technique of Affinity Chromatography.

TABLE 2

| Age (in hours) | Control - Residual Lactate (mM) | With Zinc salt - Residual Lactate (mM) |
| --- | --- | --- |
| 72 | 18.1 | 16.6 |
| 96 | 17.2 | 14.7 |
| 120 | 11.1 | 7.6 |
| 144 | 8 | 6.2 |
| 168 | 7 | 4.5 |

The control reduced the accumulation of lactate by about 61.32%, whereas the media with the added salt reduced the accumulation of lactate by about 72.89%. The present example showed further reduction in the accumulation of lactate by about 11.57% in presence of said salt.

Figure 1B:
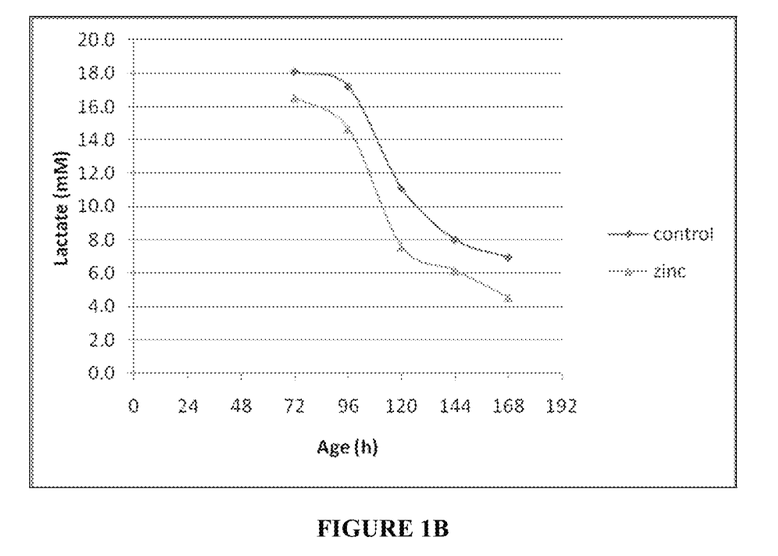
FIG. 1B illustrates the difference in level of lactate accumulation in the presence of Zinc salt Vs Control.

FIG. 1(B) illustrates the level of reduction in lactate in the culture medium.

Example 2

Example 2A

The cell culturing was performed in fedbatch mode. In the cell culture, the mammalian host cells used were Chinese Hamster Ovary (CHO) cells and HyClone CDM4NS0 culture medium was supplied initially. The CHO cells were genetically engineered to produce the Anti Her-2 antibody. The copper sulphate pentahydrate salt was added in the medium at a concentration of 0.4 mM. In contrast, there was no addition of any copper salt in the control medium. The production fermentation run started with an initial cell count of 0.3-0.45×10$^6$ cells/ml at 37±1° C., the first 3-4 days were dedicated to grow the cells in batch phase. In the next step, the temperature is lowered to 31+/−1° C. and the run is continued till 7$^{th}$ day. The below table 3 discloses the level of lactate reduced throughout the run. The produced Anti Her-2 antibody was then collected from the media using the technique of Affinity Chromatography.

TABLE 3

| Age (in hours) | Control - Residual Lactate (mM) | With Copper salt - Residual Lactate (mM) |
| --- | --- | --- |
| 72 | 18 | 16 |
| 96 | 13.1 | 11.8 |
| 120 | 8.3 | 7.4 |
| 144 | 7.4 | 6.9 |
| 168 | 8.9 | 5.6 |

The control reduced the accumulation of lactate by about 50.5%, whereas the media with the added salt reduced the accumulation of lactate by about 65%. The present example showed further reduction in the accumulation of lactate by about 14.5% in presence of said salt.

Figure 2:
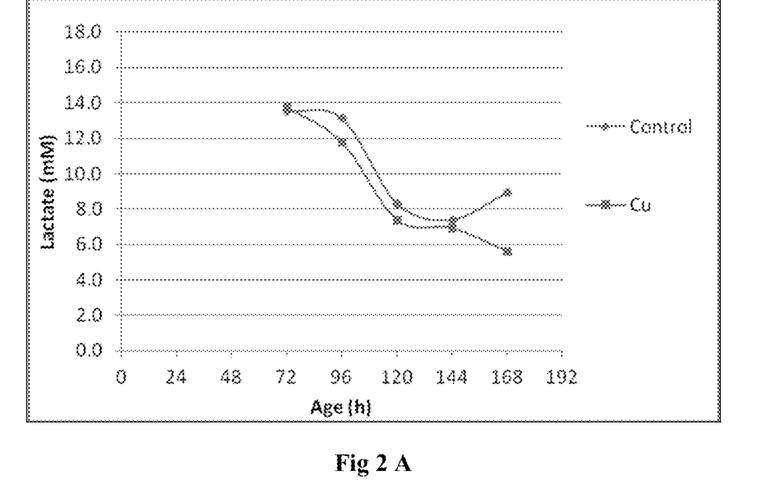
FIG. 2A illustrates the difference in level of lactate accumulation in the presence of Copper salt Vs Control.
FIG. 2B illustrates the difference in level of lactate accumulation in the presence of Zinc salt Vs Control.

FIG. 2(A) illustrates the level of reduction in lactate in the culture medium.

Example 2B

The cell culturing was performed in fedbatch mode. In the cell culture, the mammalian host cells used were Chinese Hamster Ovary (CHO) cells and HyClone CDM4NS0 culture medium was supplied initially. The CHO cells were genetically engineered to produce the Anti Her-2 antibody. The zinc sulphate hepta hydrate salt was added in the medium at a concentration of 0.4 mM. In contrast, there was no addition of any zinc salt in the control medium. The production fermentation run started with an initial cell count of $0.3$-$0.45 \times 10^6$ cells/ml at $37 \pm 1°$ C., the first 3-4 days were dedicated to grow the cells in batch phase. In the next step, the temperature is lowered to $31+/-1°$ C. and the run is continued till $7^{th}$ day. The below table 4 discloses the level of lactate reduced throughout the run. The produced Anti Her-2 antibody was then collected from the media using the technique of Affinity Chromatography.

TABLE 4

| Age (in hours) | Control - Residual Lactate (mM) | With Zinc salt - Residual Lactate (mM) |
|---|---|---|
| 72 | 18 | 16 |
| 96 | 13.1 | 11.8 |
| 120 | 8.3 | 7.4 |
| 144 | 7.4 | 6.9 |
| 168 | 8.9 | 5.6 |

The control reduced the accumulation of lactate by about 34.5%, whereas the media with the added salt reduced the accumulation of lactate by about 64.88%. The present example showed further reduction in the accumulation of lactate by about 30.38% in presence of said salt.

Figure 2B:
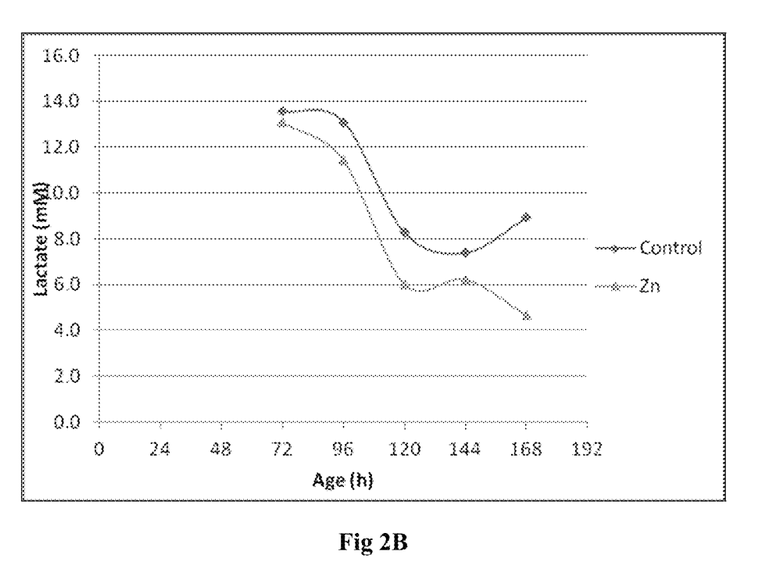

FIG. 2(B) illustrates the level of reduction in lactate in the culture medium.

Example 3

The cell culturing was performed in fedbatch mode. In the cellculture, the mammalian host cells used were Chinese Hamster Ovary (CHO) cells and HyClone CDM4NS0 culture medium was supplied initially. The CHO cells were genetically engineered to produce the Anti CD6 Antibody. The zinc sulphate hepta hydrate salt is added in the medium at a concentration of 0.4 mM. In contrast, there was no addition of any zinc salt in the control medium. The production fermentation run started with an initial cell count of $0.3$-$0.45 \times 10^6$ cells/ml at $37 \pm 1°$ C., the first 3-4 days were dedicated to grow the cells in batch phase. In the next step, the temperature is lowered to $31 \pm 1°$ C. and the run is continued till $7^{th}$ day. The below table 5 discloses the level of lactate reduced throughout the run. The produced Anti CD6 Antibody was then collected from the media using the technique of Affinity Chromatography.

TABLE 5

| Age (in hours) | Control - Residual Lactate (mM) | With Zinc salt - Residual Lactate (mM) |
|---|---|---|
| 72 | 18 | 18 |
| 96 | 11.2 | 11.2 |
| 120 | 9.8 | 6.2 |

TABLE 5-continued

| Age (in hours) | Control - Residual Lactate (mM) | With Zinc salt - Residual Lactate (mM) |
|---|---|---|
| 144 | 4.6 | 3 |
| 168 | 5.3 | 3.2 |

The control reduced the accumulation of lactate by about 70.55%, whereas the media with the added salt reduced the accumulation of lactate by about 82.22%. The present example showed further reduction in the accumulation of lactate by about 11.67% in presence of said salt.

Figure 3:
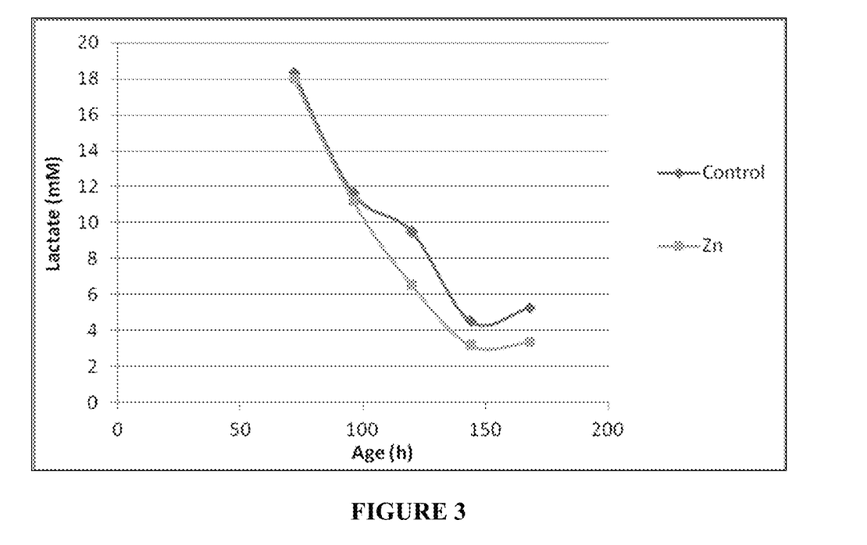
FIG. 3 illustrates the difference in level of lactate accumulation in the presence of Zinc salt Vs Control.

FIG. 3 illustrates the level of reduction in lactate in the culture medium.

Example 4

Experiment for 4(A)

The cell culturing was performed in fedbatch mode. In the cell culture, the mammalian host cells used were Chinese Hamster Ovary (CHO) cells and HyClone CDM4NS0 culture medium was supplied initially. The CHO cells were genetically engineered to produce the Anti TNF antibody. The copper sulphate pentahydrate salt is also added in the medium at a concentration of 0.4 mM. In contrast, there was no addition of any copper salt in the control medium. The production fermentation run started with an initial cell count of $0.3$-$0.45 \times 10^6$ cells/ml at $37 \pm 1°$ C., the first 3-4 days were dedicated to grow the cells in batch phase. In the next step, the temperature is lowered to $31 \pm 1°$ C. and the run is continued till $7^{th}$ day. The below table 6 discloses the level of lactate reduced throughout the run. The produced Anti TNF antibody was then collected from the media using the technique of Affinity Chromatography.

TABLE 6

| Age (in hours) | Control - Residual Lactate (mM) | With Copper salt - Residual Lactate (mM) |
|---|---|---|
| 72 | 20.8 | 20.4 |
| 96 | 21.3 | 20.3 |
| 120 | 18.2 | 16.3 |
| 144 | 15.6 | 13.2 |
| 168 | 17.6 | 14.6 |

The control reduced the accumulation of lactate by about 15.38%, whereas the media with the added salt reduced the accumulation of lactate by about 28.43%. The present example showed further reduction in the accumulation of lactate by about 13.05% in presence of said salt.

Figure 4A:
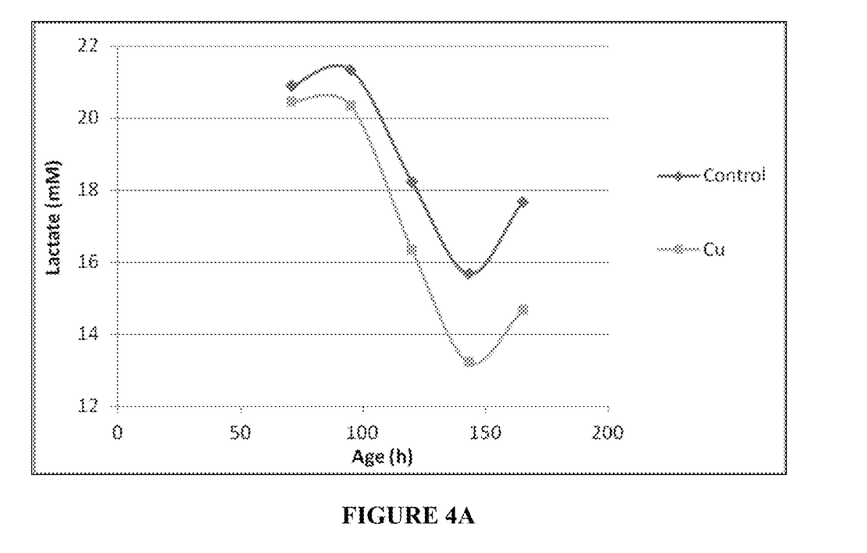
FIG. 4A illustrates the difference in level of lactate accumulation in the presence of Copper salt Vs Control.

FIG. 4A illustrates the level of reduction in lactate in the culture medium.

Experiment for 4(B)

The cell culturing was performed in a fedbatch mode. In the cell culture, the mammalian host cells used were Chinese Hamster Ovary (CHO) cells and HyClone CDM4NS0 culture medium was supplied initially. The CHO cells were genetically engineered to produce the Anti TNF antibody. The zinc sulphate hepta hydrate salt is also added in the medium at a concentration of 0.4 mM. In contrast, there was no addition of any zinc salt in the control medium. The production fermentation run started with an initial cell count of 0.3-0.45×10⁶ cells/ml at 37±1° C., the first 3-4 days were dedicated to grow the cells in batch phase. In the next step, the temperature is lowered to 31±1° C. and the run is continued till 7$^{th}$ day. The below table 7 discloses the level of lactate reduced throughout the run. The produced Anti TNF antibody was then collected from the media using the technique of Affinity Chromatography.

TABLE 7

| Age (in hours) | Control - Residual Lactate (mM) | With Zinc salt - Residual Lactate (mM) |
|---|---|---|
| 96 | 21.3 | 19.6 |
| 120 | 18.2 | 16.4 |
| 144 | 15.6 | 13.8 |
| 168 | 17.6 | 15 |

The control reduced the accumulation of lactate by about 17.37%, whereas the media with the added salt reduced the accumulation of lactate by about 23.46%. The present example showed further reduction in the accumulation of lactate by about 6.09% in presence of said salt.

Figure 4B:
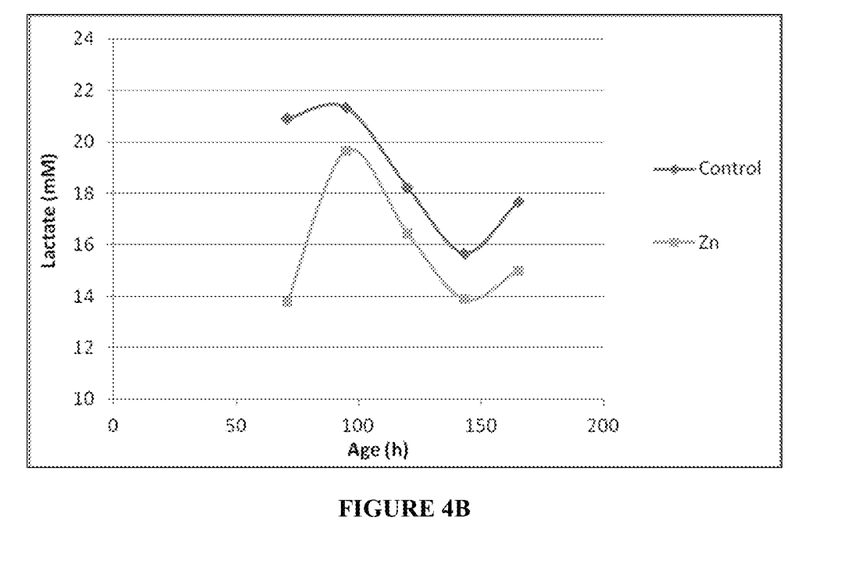
FIG. 4B illustrates the difference in level of lactate accumulation in the presence of Zinc salt Vs Control.

FIG. 4B illustrates the level of reduction in lactate in the culture medium.

Example 5

Experiment for 5(A)

The cell culturing was performed in fedbatch mode is employed. In the cell culture, the mammalian host cells used were Chinese Hamster Ovary (CHO) cells and HyClone CDM4NS0 culture medium was supplied initially. The CHO cells were genetically engineered to produce the Anti VEGF-A Antibody. The copper sulphate pentahydrate salt is also added in the medium at a concentration of 0.2 mM. In contrast, there was no addition of any copper salt in the control medium. The production fermentation run started with an initial cell count of 0.3-0.45×10⁶ cells/ml at 37±1° C., the first 3-4 days were dedicated to grow the cells in batch phase. In the next step, the temperature is lowered to 31±1° C. and the run is continued till 7$^{th}$ day. The below table 8 discloses the level of lactate reduced throughout the run. The produced Anti VEGF-A Antibody was then collected from the media using the technique of Affinity Chromatography.

TABLE 8

| Age (in hours) | Control - Residual Lactate (mM) | With Zinc salt - Residual Lactate (mM) |
|---|---|---|
| 72 | 23.3 | 23.3 |
| 96 | 16.3 | 16.3 |
| 120 | 11.8 | 10 |
| 144 | 7.2 | 5.9 |
| 168 | 4.6 | 3.4 |

The control reduced the accumulation of lactate by about 79.23%, whereas the media with the added salt reduced the accumulation of lactate by about 85.40%. The present example showed further reduction in the accumulation of lactate by about 6.17% in presence of said salt.

Figure 5A:
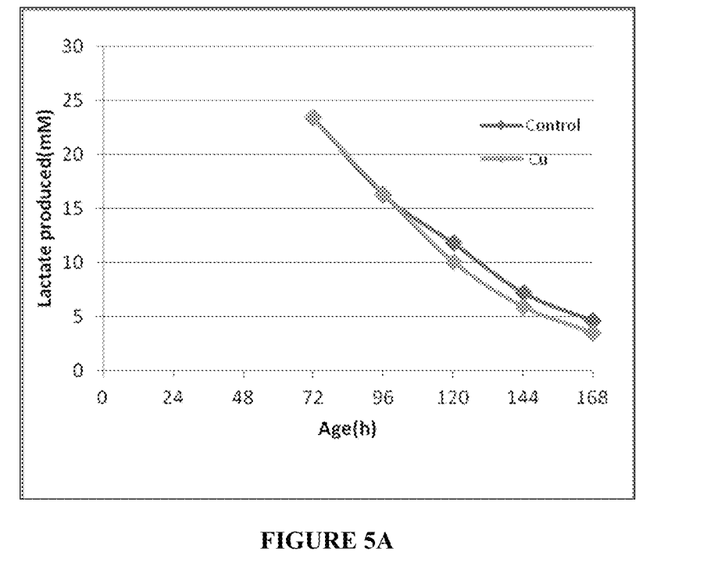
FIG. 5A illustrates the difference in level of lactate accumulation in the presence of Copper salt Vs Control.

FIG. 5A illustrates the level of reduction in lactate in the culture medium.

Experiment for 5(B)

The cell culturing was performed in fedbatch mode. In the cell culture, the mammalian host cell used were Chinese Hamster Ovary (CHO) cells and HyClone CDM4NS0 culture medium was supplied initially. The CHO cells were genetically engineered to produce the Anti VEGF-A Antibody. The zinc sulphate hepta hydrate salt is also added in the medium at a concentration of 0.2 mM. In contrast, there was no addition of any zinc salt in the control medium. The production fermentation run started with an initial cell count of 0.3-0.45×10⁶ cells/ml at 37±1° C., the first 3-4 days were dedicated to grow the cells in batch phase. In the next step, the temperature is reduced to 31±1° C. and the run is continued till 7$^{th}$ day. The below table 9 discloses the level of lactate reduced throughout the run. The produced Anti VEGF-A Antibody was then collected from the media using the technique of Affinity Chromatography.

TABLE 9

| Age (in hours) | Control - Residual Lactate (mM) | With Copper salt - Residual Lactate (mM) |
|---|---|---|
| 72 | 23.3 | 23.3 |
| 96 | 16.2 | 14.9 |
| 120 | 11.8 | 7.9 |
| 144 | 7.2 | 5.8 |
| 168 | 4.6 | 2.7 |

The control reduced the accumulation of lactate by about 79.23%, whereas the media with the added salt reduced the accumulation of lactate by about 88.41%. The present example showed further reduction in the accumulation of lactate by about 9.18% in presence of said salt.

Figure 5B:
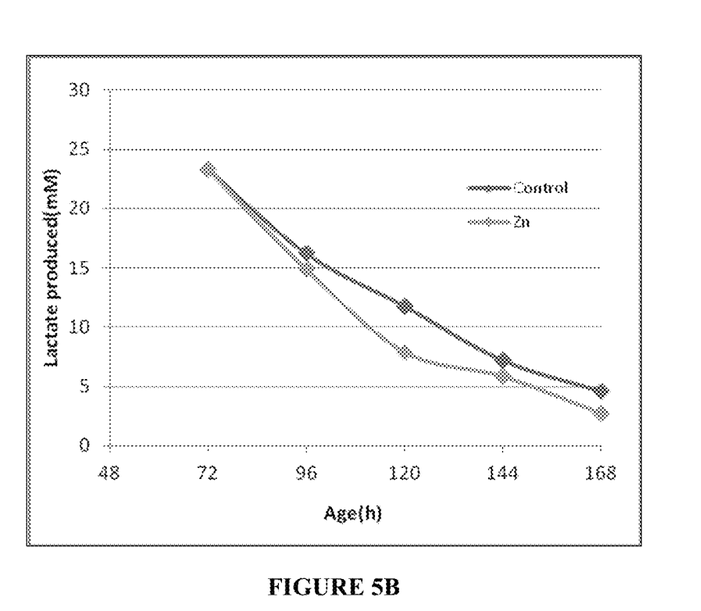
FIG. 5B illustrates the difference in level of lactate accumulation in the presence of Zinc salt Vs Control.

FIG. 5B illustrates the level of reduction in lactate in the culture medium.

Example 6

The cell culturing was performed in fedbatch mode. In the cell cultures the mammalian host cell used were Chinese Hamster Ovary (CHO) and HyClone CDM4NS0 culture medium was supplied initially. The magnesium sulphate salt which is used as a negative control is also added in the medium at a concentration of 0.4 mM. In contrast, there was no addition of any magnesium salt in the control medium. The production fermentation run started with an initial cell count of 0.3-0. 45×10⁶ cells/ml at 37±1° C., the first 3-4 days are dedicated to grow the cells in batch phase. In the next step, the temperature is reduced to 31±1° C. and the run is continued till 7$^{th}$ day.

Figure 6:
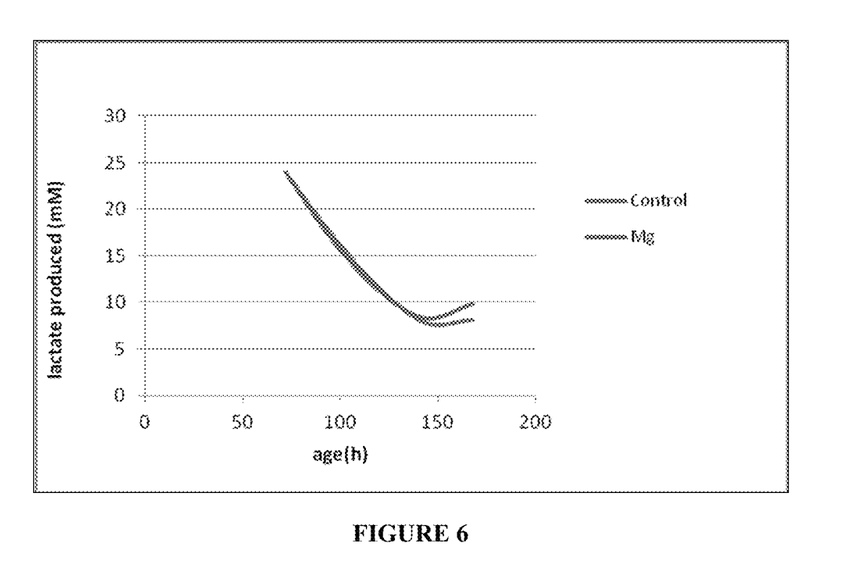
FIG. 6 illustrates the difference in level of lactate accumulation in the presence of Magnesium salt Vs Control.

FIG. 6 illustrates the level of reduction in lactate in the culture medium.

Example 7

The cell culturing was performed in fedbatch mode. In the cell cultures the mammalian host cells used were Chinese Hamster Ovary (CHO) cells and HyClone CDM4Mab culture medium was supplied initially. The zinc sulphate hepta hydrate salt are also added in the medium at a concentration of about 0.3 mM. In contrast, there was no addition of any Zinc sulphate salt in the control medium. The production fermentation run starts with an initial cell count of 0.3-0.45×10⁶ cells/ml at 37±1° C., the first 3-4 days are dedicated to grow the cells in batch phase. Next step involved in lowering the temperature to 31±1° C. and continuing the run till 7th day.

Figure 7:
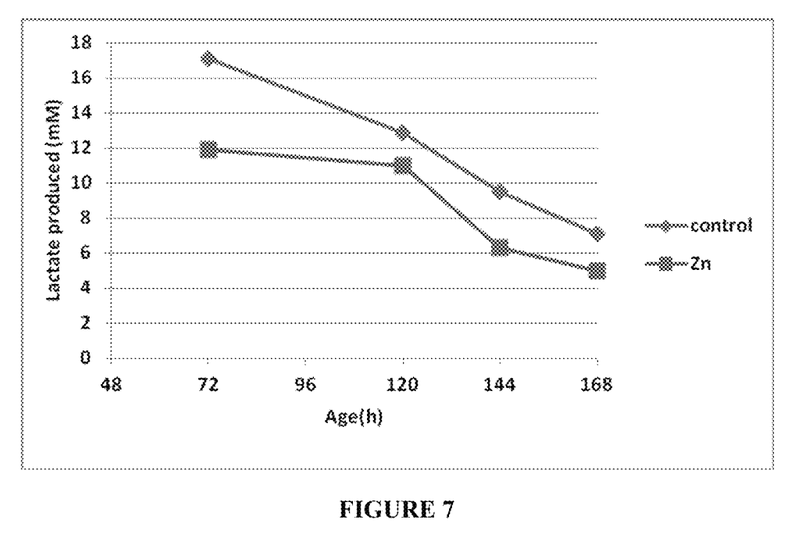
FIG. 7 illustrates the difference in level of lactate accumulation in the presence of Zinc salt Vs Control.

FIG. 7 illustrates the level of reduction in lactate in the culture medium.

We claim:

1. A method for reducing accumulation of lactate from 5% to 40% in a cell culture of Chinese Hamster Ovary (CHO cells) comprising:
   a) growing said CHO cells in culture at 37±1° C. for 3-4 days in the presence of zinc salt at a concentration ranging from 0.2 mM to 0.4 mM;
   b) reducing the temperature in the culture resulting from a) to 31±1° C. and further culturing said cells for 3-4 days, so as to reduce accumulation of lactate by 5% to 40% in the cell culture at the end of the culture period relative to a control which is not supplemental with zinc salt.

2. The method as claimed in claim 1, wherein the zinc salt is zinc sulphate.

3. The method of claim 2, wherein the zinc sulphate is zinc sulphate hepta hydrate salt.

4. The method as claimed in claim 1, wherein the culturing is carried out in a system selected from the group consisting of fed batch culturing, batch culturing, shake flasks and bioreactor.

* * * * *